(12) United States Patent
Gelissen et al.

(10) Patent No.: US 10,729,830 B2
(45) Date of Patent: Aug. 4, 2020

(54) BREAST SHIELD ARRANGEMENT FOR BREAST PUMP, BREAST PUMP AND METHOD OF OPERATION

(71) Applicant: KONINKLIJKE PHILIPS N.V., Eindhoven (NL)

(72) Inventors: Jozef Hubertus Gelissen, Eindhoven (NL); Lili-Marjan Brockhuis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 108 days.

(21) Appl. No.: 15/773,404

(22) PCT Filed: Oct. 28, 2016

(86) PCT No.: PCT/EP2016/076089
§ 371 (c)(1),
(2) Date: May 3, 2018

(87) PCT Pub. No.: WO2017/080851
PCT Pub. Date: May 18, 2017

(65) Prior Publication Data
US 2018/0318479 A1      Nov. 8, 2018

(30) Foreign Application Priority Data

Nov. 12, 2015   (EP) .................................... 15194239

(51) Int. Cl.
*A61M 1/06*        (2006.01)
*A61M 1/00*        (2006.01)
(Continued)

(52) U.S. Cl.
CPC ........... *A61M 1/066* (2014.02); *A61B 5/0082* (2013.01); *A61B 5/4312* (2013.01);
(Continued)

(58) Field of Classification Search
CPC ........ A61M 1/066; A61M 1/06; A61M 1/064; A61M 1/0031; A61M 1/062;
(Continued)

(56) References Cited

U.S. PATENT DOCUMENTS

| 8,376,986 B2 | 2/2013 | Van Schijndel |
| 8,597,234 B2 | 12/2013 | Larsson |

(Continued)

FOREIGN PATENT DOCUMENTS

| JP | 3180406 U | 12/2012 |
| WO | 0057934 A1 | 10/2000 |

(Continued)

OTHER PUBLICATIONS

Reisner, et al., Utility of the Photoplethysmogram in Circulatory Monitoring, Anesthesiology 2008: 108:950-8. (Year: 2008).*

(Continued)

*Primary Examiner* — Amber R Stiles

(57) ABSTRACT

The present invention relates to a breast shield arrangement (1) for a breast pump (2) comprising: a breast shield (3) for receiving a user's breast therein, and a sensor (4) for transmitting an input signal into the breast and receiving a corresponding reception signal in response, said reception signal indicating changes in milk flow in the breast.

15 Claims, 2 Drawing Sheets

(51) Int. Cl.
*A61B 5/00* (2006.01)
*A61B 5/024* (2006.01)
*A61B 5/16* (2006.01)

(52) U.S. Cl.
CPC ............ *A61M 1/0031* (2013.01); *A61M 1/06* (2013.01); *A61M 1/062* (2014.02); *A61M 1/064* (2014.02); *A61B 5/02416* (2013.01); *A61B 5/165* (2013.01); *A61B 5/6844* (2013.01); *A61B 5/6887* (2013.01); *A61B 2503/00* (2013.01); *A61B 2562/0247* (2013.01); *A61M 2205/3303* (2013.01); *A61M 2205/3306* (2013.01); *A61M 2205/3313* (2013.01); *A61M 2205/3334* (2013.01); *A61M 2205/50* (2013.01); *A61M 2205/502* (2013.01); *A61M 2230/06* (2013.01); *A61M 2230/20* (2013.01)

(58) Field of Classification Search
CPC .... A61M 2205/502; A61M 2205/3313; A61M 2230/20; A61M 2230/06; A61M 2205/3334; A61M 2205/3303; A61M 2205/50; A61M 2205/3306; A61B 5/4312; A61B 5/0082; A61B 2562/0247; A61B 5/6887; A61B 5/6844; A61B 2503/00; A61B 5/165; A61B 5/02416
See application file for complete search history.

(56) References Cited

U.S. PATENT DOCUMENTS

| | | | |
|---|---|---|---|
| 2005/0059928 A1* | 3/2005 | Larsson | A61B 5/053 604/74 |
| 2008/0076991 A1* | 3/2008 | Ayers | A61B 5/0205 600/324 |
| 2010/0217148 A1 | 8/2010 | Binder | |
| 2010/0312128 A1* | 12/2010 | Karst | A61B 5/026 600/506 |
| 2011/0160656 A1 | 6/2011 | Johnson | |
| 2012/0116298 A1 | 5/2012 | Van Schijndel | |
| 2014/0171917 A1 | 6/2014 | Greter | |
| 2016/0157725 A1* | 6/2016 | Munoz | A61B 5/0077 600/430 |

FOREIGN PATENT DOCUMENTS

| | | |
|---|---|---|
| WO | 2009060448 A2 | 5/2009 |
| WO | 2013093739 A1 | 6/2013 |

OTHER PUBLICATIONS http://www.who.int/topics/breastfeeding/en/ (last viewed Jun. 11, 2014).

M.W. Woolridge, The 'anatomy' of infant sucking, Midwifery, (1986) 2, 164-171.

* cited by examiner

BREAST SHIELD ARRANGEMENT FOR BREAST PUMP, BREAST PUMP AND METHOD OF OPERATION

FIELD OF THE INVENTION

The present invention relates to a breast shield arrangement for use with an expression kit of a breast pump, to a breast pump comprising such a breast shield arrangement and a method for operation of a breast pump with an according breast shield arrangement.

This application is the U.S. National Phase application under 35 U.S.C. § 371 of International Application No. PCT/EP2016/076089, filed on Oct. 28, 2016, which claims the benefit of International Application No. 15194239.8 filed on Nov. 12, 2015. These applications are hereby incorporated by reference herein.

BACKGROUND OF THE INVENTION

WO 00/57934 A1 discloses a mammary gland pump for extracting breast milk from a female breast. The mammary gland pump comprises a receiving unit configured to receive a breast therein. The receiving unit is in suction communication with a vacuum source, the suction being controlled by a micro-processor controlled electro-mechanical valve for simulating natural suckling patterns, especially suckling patterns stimulating the milk ejection reflex.

If breastfeeding is carried out, the baby's suckling pattern will trigger the milk ejection reflex, but if a mammary gland pump has to be used, the milk ejection might be not successful or not effective due to lack of correct suckling patterns. To aid the milk ejection, the teaching of the WO 00/57934 A1 proposes to arrange a sensor in the receiving unit to detect the start of milk flow from the breast. The signal of the sensor is then fed back to the micro-processor which changes the respective suckling pattern from "triggering" to "emptying".

However, the sensor is arranged in optical communication with the coupling end of the receiving unit, that is, the milk ejection is not detected until a fluid flow through the reception unit in vicinity to the sensor occurs. Due to the distance between mammary gland and sensor the detection of the milk flow and thus the adjustment of the suckling pattern are delayed. Besides, faulty measurements can occur when other fluids are present, for example sweat or water due to previous lavation of breast or receiving unit.

US 2005/0059928 A1 refers to a breast shield and to a device and method for detecting changes in a mother's breast during the expression of milk. Light is hereby conveyed to the breast, and the reflected light is received and analyzed by an optical spectrum analyzing instrument. Thus changes in the breast detectable by changes in the reflected light may be used in studying milk production and expression an may be used as a control signal in controlling a breast pump.

US 2011/0160656 A1 discloses a breast pump system with a breast pump and a breathing guidance to provide a suggested breathing pattern to the user. The system may also include a heart rate monitor for measuring the heart rate of the user, and the suggested breathing pattern may be coupled to the measured heart rate.

In US 2012/0116298 A1 a breast pump with a sensing unit is described, the sensing unit being configured to detect a physiological response from a user of the breast pump and to trigger a change in an operation of the breast pump in dependence of the detected physiological response. The sensing unit is located separate from a funnel of the breast pump.

SUMMARY OF THE INVENTION

It is an object of the present invention to provide a breast shield arrangement which allows direct detection of the beginning of the milk flow in the breast without delay and with a high degree of precision to make the use of a breast pump as comfortable as possible for a user. It is a further object of the present invention to provide a corresponding breast pump and a method of operation.

In a first aspect of the present invention a breast shield arrangement for a breast pump is presented, the breast shield arrangement comprising a breast shield for receiving a user's breast therein, and a photoplethysmographic, PPG, sensor for transmitting an input signal into the breast and receiving a corresponding reception signal in response, said reception signal comprising AC and DC components, the DC component of the reception signal comprising information on the change of bulk absorption in the breast indicating changes in milk flow in the breast. The breast shield arrangement of the invention is an easy to use and precise instrument to help lactating women to experience a relaxed effective milk ejection with high yield at a low stress level.

In another aspect of the invention a breast pump is presented, comprising a breast shield arrangement, a pressure source in air-ducting connection to the breast shield for generating increased or reduced pressure in the breast shield to extract breast milk, and a control unit for controlling the pressure source on the basis of the reception signal from the sensor comprising AC and DC components, the DC component of the reception signal comprising information on the change of bulk absorption in the breast. Advantageously, the breast shield arrangement of the invention can be used to be connected to any breast pump with a suitable control unit since the values measured by the sensor are simple data which do not need special hard- or software but only a small signal processing unit which can be fitted to any breast pump with changeable suction modi. The present invention may also be used with different types of breast pumps, i.e. breast pumps of a first type using negative pressure or suction (e.g. vacuum pumps) and breast pumps of a second type using positive pressure.

In a further aspect of the present invention a method for operating a breast pump is presented, said breast pump comprising a breast shield arrangement, a pressure source and a control unit, the method comprising:
 transmitting an input signal into the breast,
 receiving a corresponding reception signal in response, said reception signal comprising AC and DC components, the DC component of the reception signal comprising information on the change of bulk absorption in the breast indicating changes in milk flow in the breast,
 evaluating said reception signal, and
 controlling the pressure source on the basis of the evaluated reception signal.

An advantage of the operation method according to the invention is that the user of the breast pump does not have to observe herself the start of the milk expression but can rely on a very precise measurement with direct control of the suction mode of the pressure source. Erroneous measurements are nearly impossible, making the use of the breast pump simple and comfortable for the user.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, breast pump, computer program and medium have similar and/or identical preferred embodiments as the claimed breast shield arrangement, in particular as defined in the dependent claims and as disclosed herein.

The sensor is an optical sensor, in particular a photoplethysmographic, PPG, sensor. PPG sensors are known from the arts and thus offer a cheap and easy to use possibility to obtain precise values about the start of the milk ejection reflex.

Preferably, the PPG sensor is arranged in contact with the skin of the breast or in close vicinity to the skin, in particular at a distance of less than 1 cm. Thus, precise measurements with reliable values at a very short reaction time in changing the operational mode of the pressure source of the breast pump can be carried out.

According to another advantageous embodiment of the invention, the sensor is a remote photoplethysmographic, rPPG sensor, in particular a camera. The camera can be arranged elsewhere outside the breast shield, thus improving the comfort in use of the breast pump due to absence of further objects in vicinity of the possibly very algesic breast.

Alternatively, the sensor can also be a laser speckle interferometer.

Preferably, the sensor is arranged in or on the breast shield, in particular on an inner or outer surface of the breast shield or embedded in the material of the breast shield. By adequate arrangement of the sensor, the danger of damage to the sensor or injury to the user can be minimized.

In an advantageous embodiment of the invention the breast pump can comprise a user interface for conveying information, guidance and recommendations to the user of the breast pump. This can especially be helpful if the user is in a hurry, insecure or suffers from pain when using the breast pump. Any of these obstacles can be for example relieved by guidance to controlled breathing and thus finding into a state of relaxation supporting the triggering of the milk ejection reflex and the effective emptying of the breast.

Preferably the breast pump comprises a signal processing unit which is configured to analyse AC and DC components of said reception signal of the PPG or remote PPG sensor. The signal processing unit can be a simple and cheap assembly which does not need to be complex in hard or software since only simple comparisons of values have to be carried out. It can be retrofitted to known breast pumps.

According to an advantageous embodiment of the invention the signal processing unit is configured to evaluate the DC component of the reception signal comprising information on the change of bulk absorption in the breast, in particular on the increase of fluid due to the start of milk flow in the breast, and generate an according feedback signal for adjustment of the function of the pressure source. The DC component of the signal is easy to obtain from the reception signal and can be analysed by simple means.

The signal processing unit is preferably configured to detect the increase of fluid in the breast by comparison of the value of the DC component to a predetermined threshold value. The threshold values can be chosen from calibration measurements or from medical evaluations over certain shares of the female population.

According to yet another preferred embodiment, the signal processing unit is further configured to evaluate the AC component of the reception signal comprising information on vital signs, in particular on the heart-rate. The vital signs can be used to control the mental state of the user and in case of need a recommendation or helpful advice can be generated on base of the vital signs.

Preferably, the signal processing unit is configured to generate a feedback signal containing the heart-rate information contained in the AC component and/or recommendations or guidance based on the analysis of the heart-rate information of the AC component and to transmit the feedback signal to the user interface. The user which might be stressed by use of the breast pump has then the chance to relax by controlling her breath or similar relaxation techniques proposed by the user interface.

In a preferred embodiment, the proposed method comprises:

positioning of the breast shield arrangement with the sensor on the user's breast, operating the pressure source of the breast pump in a first operation mode, emitting light from at least one light source in the sensor into the tissue of the breast, receiving a respective reception signal in a detector in the sensor, analysing the AC and DC components of the reception signal in the signal processing unit, and feeding back a signal to the control unit with either changing the first operation mode of the pressure source into a second operation mode different from the first operation mode if a threshold value is exceeded, or operating the pressure source in unchanged mode if the threshold value is not exceeded.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE EMBODIMENTS

Figure 1:
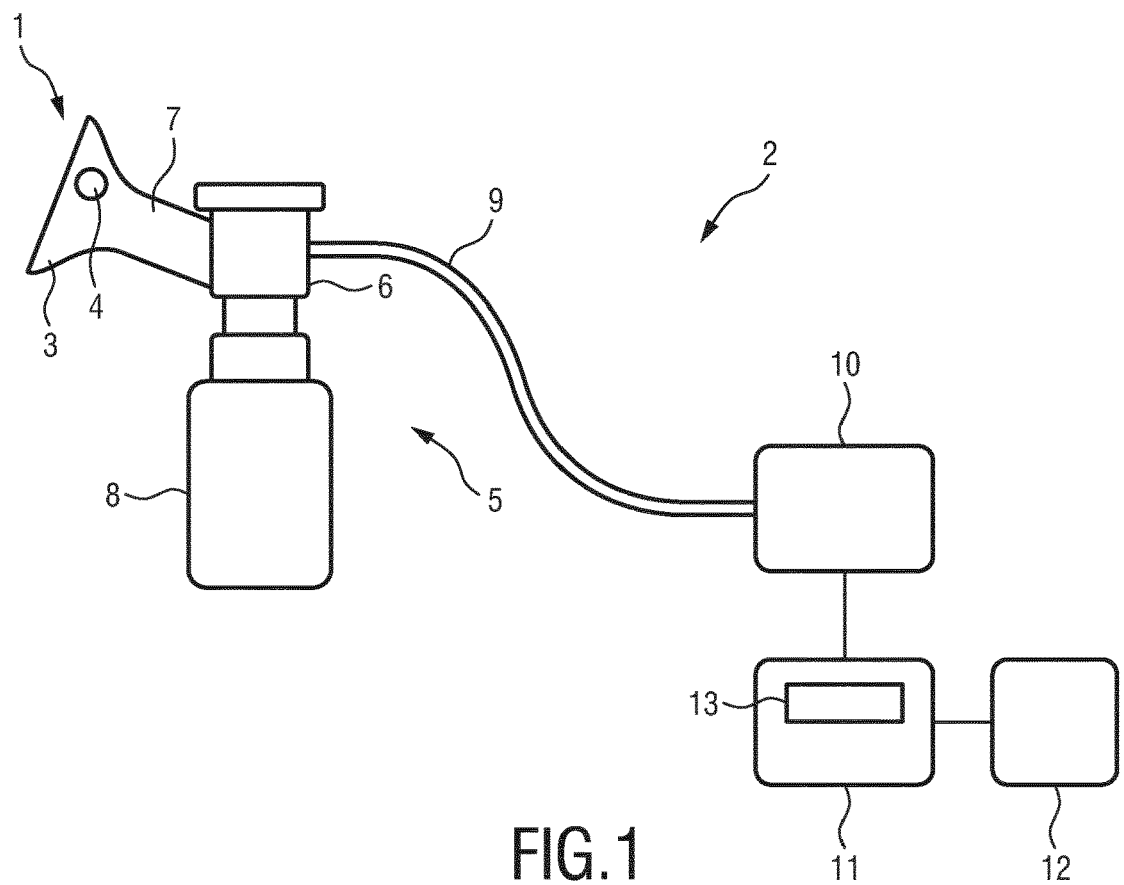
FIG. 1 shows an embodiment of a breast pump comprising a breast shield arrangement according to the invention.

FIG. 1 shows a first embodiment of a breast shield arrangement 1 for a breast pump 2 according to the invention. The breast shield arrangement 1 comprises a funnel shaped breast shield 3 which is configured to receive a user's breast therein. The breast shield 3 can be formed from any suitable resilient material like polyurethane or silicone. Since breast shields 3 are commonly known in the art, further detailed descriptions about general form and function are deemed to be not necessary here.

According to the invention, the breast shield 3 comprises a sensor 4 which is arranged in or on the breast shield 3. Further details about the arrangement of the sensor 4 will be explained below with reference to FIG. 2.

The breast shield arrangement 1 is connected to an expression kit 5 via a connecting end 7. The expression kit 5 comprises a receptacle 6, to which the breast shield 3 is connected. The receptacle 6 is configured to receive the milk expressed from the user's breast and to guide it towards a container 8 which is also connected to the receptacle 6. In the receptacle 6 further components can be housed which are necessary for operation of the breast pump, e.g. a valve assembly (not shown) which allows controlled suction functionality.

The breast pump 2 further comprises an air-ducting connection 9 to a vacuum source 10. The vacuum source 10, used in this embodiment as one exemplary embodiment of a pressure source, is configured to apply negative pressure to the breast shield 3 aided by the at least one valve assembly in the receptacle 6. Alternatively, the at least one valve assembly can be arranged in a housing of the vacuum source 10 or in the air-ducting connection 9.

The vacuum source 10 can be any suitable pumping mechanism like a mechanical or an electrical pump.

The breast pump 2 further comprises a control unit 11 in operative interaction to the vacuum source 10. The control unit 11 is responsible for the control of the function of the vacuum source 10 in dependency from signals received from the sensor 4 in the breast shield 3.

Preferably, the breast pump further comprises a signal processing unit 13, e.g. as part of the control unit 11 (as shown in FIG. 1) or as a separate component. The signal processing unit 13 receives the signals from the sensor 4, evaluates the information contained therein and generates feedback signals for the adaption of the function of the vacuum source.

Further, a user interface 12 which can be any or a combination of a speaker, a vibrational signal unit or an optical display may be provided in connection with the control unit 11. The user interface 12 conveys information to the user of the breast pump 2 as described later in more detail.

Figure 2:
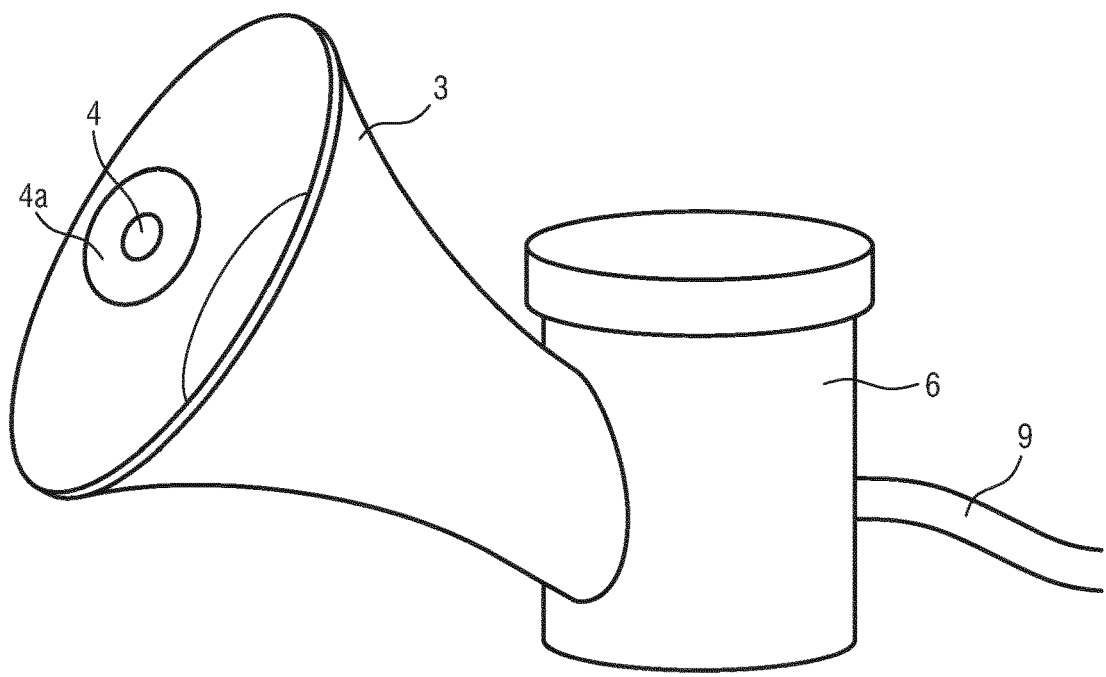
FIG. 2 shows a detailed illustration of an embodiment of a breast shield arrangement according to the invention.

Turning now to FIG. 2, the embodiment of the breast shield arrangement 1 with the sensor 4 on the breast shield 3 is described in more detail. Preferably, the sensor 4 takes the shape of a thin annular element, since an annular form is easy to handle and contains no sharp angles with the danger of injury of the user. However, any other form of the sensor 4 is possible.

The sensor 4 might be arranged on an inner or outer surface of the breast shield 3. Since the sensor 4 is an optical sensor as will be described in more detail hereinafter, arrangement on the outer surface is only possible when the material of the breast shield 3 is translucent. However, arrangement on the outside would be preferable since the danger of injury of the user or of damage of the sensor 4 is minimized.

Alternatively the sensor 4 can also be embedded in the material of the breast shield 3. "Embedded" in this respect is meant to describe an arrangement of the sensor 4 either in a recess of the breast shield 3 wherein the recess is open to at least one surface of the breast shield 3, or completely covered with the breast shield's material. The latter could for example be accomplished by moulding or casting.

In case the sensor 4 is arranged on an inner surface of the breast shield 3, it comprises preferably a sensor pad 4a which surrounds the sensor 4 and spaces the sensor 4 from the skin of the user. The background of this additional sensor pad 4a is the observation, that a sensor 4 which is directly placed on the user's skin might lead to biased measurement values due to the pressure of the sensor 4 on the skin. The thickness of the sensor pad 4a should be sufficiently small to make sure that the sensor 4 remains in close proximity of the skin of the user. Preferably, the distance between the sensor 4 and the skin of the user is less than 1 cm, particularly preferable less than 0.5 cm.

The sensor 4 is in operative interaction with the control unit 11 (connection not shown in FIG. 1). Measured values of the sensor will be delivered to the control unit 11 and processed in the signal processing unit 13.

The sensor 4 is an optical sensor, especially a photoplethysmographic sensor. The photoplethysmographic sensor 4 will be referred to as PPG sensor 4 hereinafter. PPG sensors 4 are known in the arts, they are especially used for measurement of the oxygen saturation of the blood. To facilitate the understanding of the invention, the measurement principle of a PPG sensor 4 is shortly described in the following.

At least one light source, for example a light emitting diode, emits light which is introduced into the tissue of the respective body part. Normally, for measurement a thin part of the body like a finger tip or the earlobe is used. In these cases, the light from the light source passes through the whole body part's tissue and is detected by at least one photodetector which is arranged opposite to the light source with the body part between light source and detector. The amount of light transmitted through the tissue is measured by the photodetector and compared to the emitted light from the light source. The difference between the values is a measure for the bulk absorption and the fluid contents of the respective tissue. From this, the degree of oxygen saturation in the blood which flows through the tissue can be calculated. If the saturation is higher the amount of transmitted light will be different compared to a lower saturation due to differences in the bulk absorption and the fluid contents.

In case of the breast shield arrangement 1 for the breast pump 2 described above it is not possible to transmit light through the breast tissue to a detector which is arranged opposite to the light source, since the amount of tissue is too large to be rayed completely. In this case, the light is emitted into the tissue and the amount of light reflected in the tissue is measured by the detector. The sensor 4 thus comprises at least one light source and at least one photodetector adjacent to each other with the light source sending light into the breast tissue and the detector detecting the amount of light reflected in the breast tissue.

Accordingly, the amount of reflected light will vary with varying degree of fluid contents in the breast tissue. On the one hand, the breast tissue is supplied with blood, on the other hand the breast tissue of women, who have born recently, produces breast milk enabling the women to feed their children by breastfeeding. Thus, a milk flow in the breast tissue will be detectable by a change in fluid contents of the breast tissue.

To start milk ejection from the breast, the so-called milk ejection reflex (MER) has to be triggered. Triggering normally works by suckling action of the child on the nipple of the feeding woman. By this suckling action, the hormone oxytocin is emitted into the blood and triggers milk ejection when detected by receptor cells in the breast tissue. In case of a nursing woman, the milk ejected from the breast leads to a different suckling action of the child. If a nursing mother is forced however to refrain from breastfeeding and instead has to collect breast milk by a breast pump 2, the milk ejection normally has to be monitored by the user of the breast pump 2 directly. The state of the art only offers breast pumps which detect the presence of milk flow outside the breast tissue. In these breast pumps, erroneous measurements and delays in adaption of the functionality of the breast pump are observed.

The breast pump 2 according to the invention offers by use of the sensor 4 a direct detection of the start of the milk ejection in the breast tissue even before the milk ejection outside the breast is detected. Thus, the pressure source 10 can react directly on the start of the milk expression. The breast pump 2 is operated at a certain suction pressure and suction frequency until the milk ejection is detected by the sensor 4. The signal received due to the change in fluid contents in the breast tissue is sent to the control unit 11, analysed by the signal processing unit 13 and fed back to the vacuum source 10 to change the suction modus.

Figure 3:
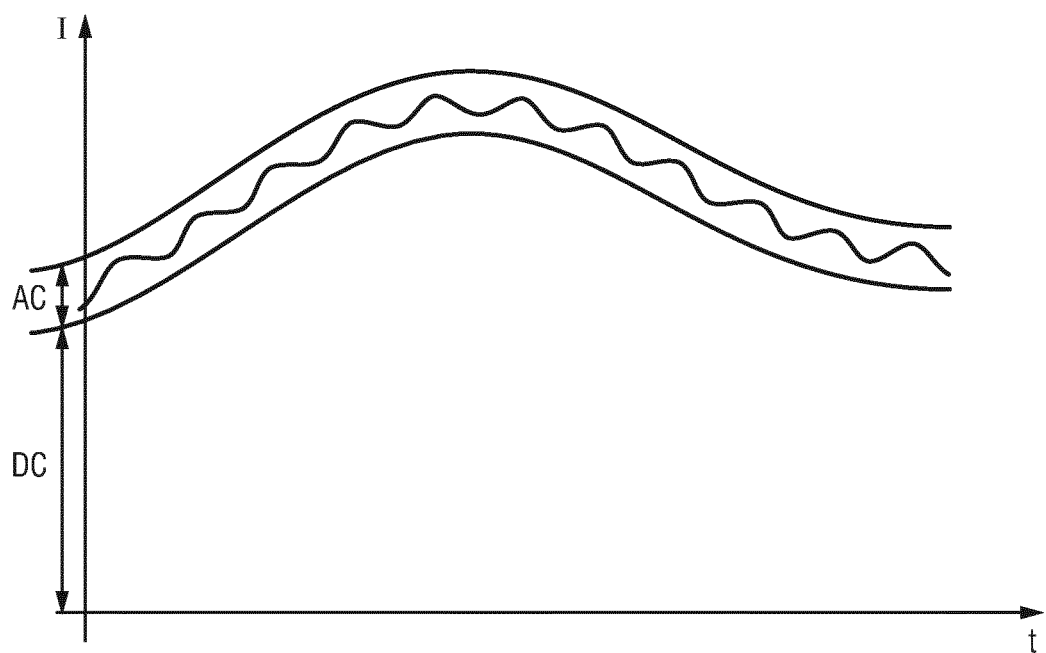
FIG. 3 shows a schematic diagram of the AC and DC components of the signal derived from an optical sensor in a breast shield arrangement according to FIG. 1 or 2.

For the analysis of the signals, a known technique is used. The signal detected by the photodetector is split up in two components, the AC component and the DC component and the different components analysed on the information contained therein. A schematic diagram of the components is shown for reference in FIG. 3.

The AC component mainly contains information on vital signs, especially on the heart rate. The DC component contains information on the bulk reflection in the breast tissue. The ratio AC/DC is called the modulation and reflects, as a percentage, the amount which can be used for derivation of the heart rate.

For the inventive breast shield arrangement 1 for a breast pump 2, the DC component is the relevant measure. When the milk ejection starts, the fluid content in the breast tissue increases compared to the normal status when the breast tissue is only supplied with blood. The increase in signal reflects the presence of both fluids, namely blood and milk.

Figure 4:
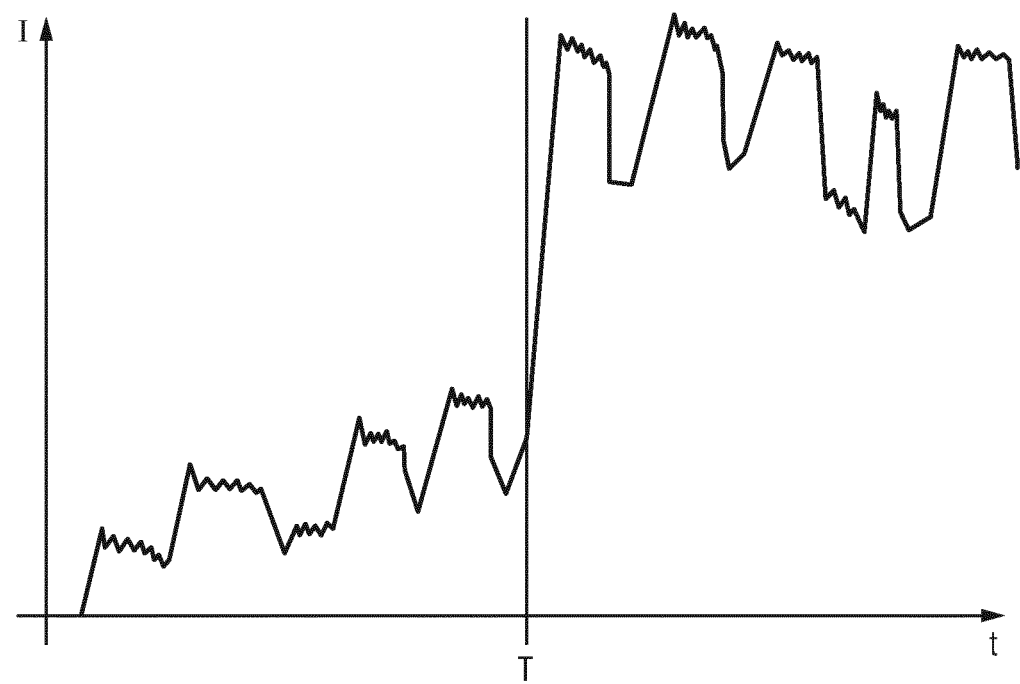
FIG. 4 shows a schematic diagram of the signal according to the start of the milk ejection in a female breast.

The detectable increase in the DC component is shown schematically with reference to FIG. 4. The intensity of the PPG signal (denoted I on the y-axis) during operation of the breast pump 2 changes periodically over time (denoted t on the x-axis) with the suction cycles of the vacuum source 10. A strong increase is perceivable at time T within the diagram of FIG. 4. This increase is the change in fluid contents in the breast tissue and the resulting different absorption of light. This jump in the signal is detectable by the sensor 4 and used to control the suction mode of the vacuum source 10.

In FIG. 4, also the user's heart rate is still visible as small peaks on the larger sine waves.

The signal processing unit 13 uses the jump in the DC component to determine the start of the milk expression. The method of analysis can for example comprise use of a boundary or threshold which has to be exceeded to change the suction mode of the vacuum source. For example, an increase of the DC-value by 5% could result in the change of the suction mode. Alternatively, other user specific values could be used which can take into account e.g. the breast size or calibration measurements from earlier pumping cycles and so on.

The user of the breast pump 2 thus has no necessity to act on her own account when feeling the milk expression but simply has to rely on the automated action of the breast pump 2.

The sensor 4 does not necessarily have to be a normal PPG sensor, but can also be a remote PPG sensor which also works from a certain distance, or alternatively also a laser-speckle interferometer. Both techniques are known in the art and thus do not have to be described in more detail here. The relevant value the increase in the DC component is however present in the values of all sensor types referred to.

As already mentioned with reference to FIG. 1, a user interface 12 can be present, which is connected to the control unit 11. The user interface 12 can comprise for example a speaker, a vibrational unit and/or a display. The user interface 12 is suitable to convey information to the user of the breast pump 2, especially information derived from the above-mentioned AC component of the signal detected by the sensor 4. The AC component of the signal comprises mainly information on the vital signs of the user, for example the heart rate, and can be used to generate a feedback for stress relaxation.

Young women nourishing for the first time often are insecure and nervous when using a breast pump 2. Thus, the heart rate of these users will be high and reflect their mental state. On the other hand, this nervousness might lead to bad results when trying to extract breast milk from the breast. The signal processing unit 13 of the control unit 11 can analyse the AC component of the signal in addition to the DC component and convey useful information contained therein via the user interface 12 to the user. For example, it is possible that a recommendation is generated and presented to the user to help to decrease the heart rate by a special breathing technique. If the breathing technique is successful, the decrease in heart rate is also fed back to the user thus improving the comfort and ease of the user. Stress relaxation generally will help to increase the flow of breast milk and thus can improve the yield.

To further improve the precise function of the breast pump 2 it is possible to arrange a second sensor, e.g. in form of a flow sensor, for example in the expression kit 6 or in the air-ducting connection 9. By way of the flow sensor, an additional measure about the time and amount of milk extraction from the breast can be gained and used to control the functionality of the breast pump 2, for instance by generating a control signal for the breast pump based on the reception signal of the sensor 4 and the signal from the additional flow sensor.

Yet another implementation of the invention is the application of the sensor in combination with a positive pressure pump instead of a vacuum pump applying negative pressure or suction to the breast. Although this may require a different connection of the air ducting to the breast shield, the sensor provided according to the invention can be used with the same or similar measurement function and with similar results.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A breast shield arrangement for a breast pump comprising:

a breast shield configured to:
  receive a user's breast therein, and
an optical sensor configured to:
  transmit an input signal into the breast; and
  receive a corresponding reception signal in response, said reception signal comprising an AC component and a DC component;
  evaluate the DC component of the corresponding reception signal for a change in the DC component;
  determine from the change in the DC component an indication of a milk flow; and
  provide a feedback signal in response to the determination of milk flow based on the change in the DC component indicating an increase in a value of the DC component.

2. The breast shield arrangement according to claim 1, wherein the PPG sensor is arranged in one of: contact with the breast and in close vicinity to the breast.

3. The breast shield arrangement according to claim 1, wherein the sensor is a remote sensor.

4. The breast shield of claim 3, wherein the remote sensor is a camera.

5. The breast shield arrangement according to claim 1, wherein the sensor is one of a: photoplethysmographic sensor and a laser speckle interferometer sensor.

6. The breast shield arrangement according to claim 1, wherein the sensor is arranged in one of: on an inner surface of the breast shield and embedded in a material of the breast shield.

7. A breast pump device comprising
a breast shield configured to:
  receive a user's breast therein, and
a sensor configured to:
  transmit an input signal into the breast; and
  receive a corresponding reception signal in response to the transmitted input signal, said reception signal comprising an AC component and a DC component;
  evaluate the DC component of the corresponding reception signal for a change; and
  determine from the change in the DC component an indication of a milk flow; and
  provide a feedback signal in response to the determination of milk flow based on the change in the DC component indicating an increase in a value of the DC component;
a pressure source, connected to the breast shield, configured to:
  generate one of: increased and reduced pressure in the breast shield, and
a control unit configured to:
  receive the feedback signal; and
  control the pressure source on the basis of the received feedback signal in a manner to extract milk from said breast by increasing and decreasing the pressure applied to the breast shield.

8. The breast pump device according to claim 7, further comprising:
a user interface configured to:
  convey at least one of: information, guidance and recommendations to the user of the breast pump.

9. The breast pump device according to claim 7, further comprising:
a signal processing unit configured to analyse said AC component and said DC component of said reception signal.

10. The breast pump device according to claim 9, wherein the signal processing unit is configured to:
evaluate the DC component of the reception signal comprising information on the change of bulk absorption in the breast, said change of bulk absorption comprising an increase of fluid from said breast; and
generate said feedback signal for adjustment of the function of the pressure source.

11. The breast pump device according to claim 9, wherein the signal processing unit is configured to:
detect an increase of fluid from the breast by comparison of the DC component to a predetermined threshold value.

12. The breast pump device according to claim 9, wherein the signal processing unit is configured to:
evaluate the AC component of the reception signal comprising information on vital signs, said vital signs comprising at least a heart rate.

13. The breast pump device according to claim 12, wherein the signal processing unit is configured to:
generate at least one of: a feedback signal containing the heart-rate information contained in the AC component and one of: a recommendation and a guidance based on an analysis of the heart-rate; and
transmit the feedback signal containing one of: the heart rate information and the guidance to the user interface.

14. A method for operating a breast pump device, the method comprising:
transmitting an input signal into a breast,
receiving a reception signal in response to the input signal, said reception signal comprising an AC component and a DC component, the DC component comprising information on a change of bulk absorption in the breast, wherein said change of bulk absorption indicating changes in milk flow in the breast,
evaluating said reception signal for a change in the DC component, and
controlling a pressure source on the basis of the evaluated reception signal, wherein a pressure provided to the breast is one of: increased and decreased.

15. A computer program comprising program code means for causing a computer to carry out the steps of the method according to claim 14 when said computer program is carried out on a computer.

* * * * *